United States Patent [19]

Hefner, Jr.

[11] Patent Number: 4,578,439

[45] Date of Patent: Mar. 25, 1986

[54] STYRYL PYRIDINE CYANATES, STYRYL PYRAZINE CYANATES AND POLYMERS THEREOF

[75] Inventor: Robert E. Hefner, Jr., Lake Jackson, Tex.

[73] Assignee: The Dow Chemical Company, Midland, Mich.

[21] Appl. No.: 639,036

[22] Filed: Aug. 9, 1984

[51] Int. Cl.$^4$ .................. C08L 61/020; C08G 8/28
[52] U.S. Cl. ..................... 525/509; 525/510; 525/517; 525/518; 525/519; 528/246; 528/248; 528/252
[58] Field of Search ............... 525/509, 510, 517, 518, 525/519; 528/248, 246, 252

[56] References Cited

U.S. PATENT DOCUMENTS

| | | | |
|---|---|---|---|
| 3,994,862 | 11/1976 | Ropars et al. ................ | 260/67.5 |
| 4,163,740 | 8/1979 | Malassine et al. ............ | 260/31.2 N |
| 4,362,860 | 12/1982 | Ratto et al. .................. | 528/248 |

OTHER PUBLICATIONS

Ming-ta S. Hsu, John A. Parker, Timothy S. Chen and Alvin H. Heimbuch, *Technology Vectors*, vol. 29, pp. 1034–1042 (1984), "Vinylstrylpyridine-Modified Bismaleimide Composite Resins", published by Society for Advancement of Material & Process Engineering.

Ming-Chien Chiang and Walter H. Hartung, *Journal of Organic Chemistry*, vol. 10, pp. 21–25 (1945), "Synthesis of Some Stilbazole Derivatives".

Bramsch, *Chemische Berichte*, vol. 42, pp. 1193–1197 (1909), "Condensations of γ-Picoline, α,α′-Lutidine and Symmetrical Collidine with Piperonal and Salicylaldehyde".

Franke, *Chemische Berichte*, vol. 38, pp. 3724–3728 (1905), "Effect of 2,5-Dimethylpyrazine on Aldehydes".

Yan, Hoh–Jiear, "Synthesis, Characterization and Thermal Stability of Styrylpyridine Based Polymers", pp. 100–109, copyright 1983, University Microfilms International, 300 N. Zeeb Road, Ann Arbor, Michigan.

Yan, H. J. and Pearce, Eli M., Polymer Preprints, vol. 25, No. 1, p. 135 (1984), "Studies on Styrylpyridine Based Polymers".

Yan, Hoh–Jiear, Eli M. Pearce and B. J. Bulkin, "Styryl–Pyridine Based Epoxy Resins: Synthesis and Characterization", *Organic Coatings and Applied Polymer Science Proceedings*, vol. 46, pp. 482–488 (1982) published by American Chemical Society.

*Primary Examiner*—Theodore E. Pertilla
*Attorney, Agent, or Firm*—James G. Carter

[57] ABSTRACT

Styryl pyridine and styryl pyrazine cyanates are prepared by cyanating the reaction product of (A) a substituted pyridine and/or pyrazine with (B) a substituted aromatic aldehyde with the proviso that at least one of the components (A) or (B) contains a hydroxyl group which is susceptible to being cyanated. These cyanates can be homopolymerized or copolymerized with other materials to produce polymers having excellent high temperature resistance, good mechanical strength and excellent processability.

33 Claims, No Drawings

STYRYL PYRIDINE CYANATES, STYRYL PYRAZINE CYANATES AND POLYMERS THEREOF

BACKGROUND OF THE INVENTION

This invention relates to thermosettable styryl pyridine or pyrazine cyanate compositions which are prepared using a hydroxy functional styryl pyridine or pyrazine (HSP) precursor.

Polystyryl pyridines have been recently developed for use in applications requiring light weight and a high degree of fire resistance. Typical of these applications are composite materials for use in both aircraft and spacecraft. U.S. Pat. Nos. 3,994,862 and 4,163,740 disclose the preparation of said thermosettable polystyryl pyridines. Polystyryl pyridines are not, however, without problems. The condensation curing reaction to provide a polystyryl pyridine evolves water, hence voids and bubbles are typically present in the cured products. These defects are deleterious to the mechanical properties of the cured product. Reactivity of the styryl pyridine compositions is poor, with prolonged cure temperatures of 250° to 300° C. or higher being required. Finally, solubility of the styryl pyridine compositions in organic solvents is low and high melting points are typical hence conventional processing, such as impregnation of a fiberglass mat by hot melt or solvent impregnation techniques is extremely difficult.

More recently, vinyl styryl pyridines and vinyl polystyryl pyridines have been developed, for example as taught by U.S. Pat. No. 4,362,860. Said vinyl styryl pyridine compositions provide some improvement in reactivity, being initially cured at temperatures of 150° to 200° C., however, many of the aforementioned problems remain.

Various other styryl pyridine compositions are known, however, these compositions typically possess the aforementioned problems.

The present invention concerns thermosettable styryl pyridine cyanate compositions which overcome many of the deficiencies of known styryl pyridine compositions. The styryl pyridine cyanate compositions are low melting, many being liquids at room temperature (25° C.). Solvent solubility in a wide range of conventional organic solvents is typically high. Curing does not evolve gaseous products, such as water vapor, thus void-free cured products, such as castings and composites (laminates), are readily obtained. All of these property improvements are obtained without a loss in thermal stability. In fact, in many cases, char yields for the cured styryl pyridine cyanate compositions are higher than those obtained for the cured hydroxy functional styryl pyridine (HSP) precursor.

This invention also relates to certain copolymerizable mixtures of the styryl pyridine cyanate compositions and the thermoset copolymers thereof. Said compolymerizable mixtures frequently provide improved processability and reactivity while the thermoset copolymers often possess much higher mechanical strength than that of the thermoset styryl pyridine cyanate compositions, per se.

SUMMARY OF THE INVENTION

One aspect of the present invention concerns styryl pyridine cyanate or styryl pyrazine cyanate compositions resulting from cyanating a product resulting from reacting (A) at least one of
(1) one or more pyridine compounds represented by the formula

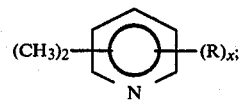

(2) one or more pyrazine compounds represented by the formula

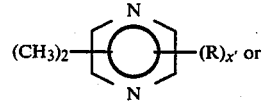

(3) a mixture of 1 and 2; with
(B) a substituted aromatic aldehyde represented by the formula

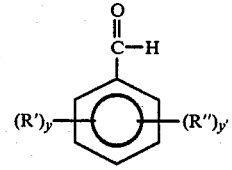

wherein each R is independently hydrogen, hydroxyl, methyl or ethyl; each R' is independently a hydroxyl or a

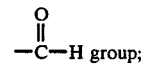

each R" is independently hydrogen, methyl or ethyl; x has a value of 3; x' has a value of 2; y has a value of 1 or 2; y' has a value of 3 or 4; the sum of y and y' has a value of 5; and with the proviso that at least one of R and R' is a hydroxyl group and wherein (i) components (A) and (B) are employed in quantities which provide the resultant reaction product with a reacted molar ratio of (B) to (A) of from about 0.33:1 to about 4:1, preferably from about 0.5:1 to about 4:1, most preferably from about 0.7:1 to about 3:1 and (ii) at least about 1, preferably from about 20 to 100, most preferably from about 30 to about 75 percent of the rings in the resultant reaction product of (A) and (B) contain at least one hydroxyl group which is susceptible to being cyanated.

Another aspect of the present invention pertains to homopolymers or copolymers of the aforementioned styryl pyridine cyanates and styryl pyrazine cyanates.

A further aspect of the present invention pertains to polymerizable mixtures of (A) at least one of the aforementioned styryl pyridine cyanates and/or styryl pyrazine cyanates; and
(B) at least one material selected from
(1) styryl pyridines and/or prepolymers or polymers thereof;
(2) vinyl styryl pyridines and/or prepolymers or polymers thereof;

(3) alkenyl phenyl cyanates;
(4) dicyanates and/or polycyanates;
(5) bismaleimides and/or polymaleimides;
(6) epoxy resins;
(7) alkenyl phenol capped styryl pyridines and/or prepolymers or polymers thereof; or
(8) mixtures thereof in any proportion and combination.

Another aspect of the present invention pertains to polymers and/or cured products of the aforementioned polymerizable and/or curable mixtures.

A further aspect of the present invention pertains to articles prepared from the aforementioned polymers and/or cured products.

DETAILED DESCRIPTION OF THE INVENTION

The styryl pyridine or pyrazine cyanate compositions of the present invention are prepared by reacting a hydroxyl functional styryl pyridine or pyrazine precursor with a cyanogen halide. The precursor compositions can be monomeric, oligomeric or polymeric. The precursor compounds are prepared by condensing in the presence of an acidic catalyst compounds represented by formulas I and II or mixture thereof with a substituted aromatic aldehyde represented by formula III with the proviso that at least one of the compounds represented by formulas I, II and III contains an aromatic hydroxyl group.

Suitable acidic catalysts which can be employed include, for example, sulfuric acid, hydrochloric acid, zinc chloride, acetic anhydride, aluminum trichloride, toluenedisulfonic acid, trichloroacetic acid, acetic acid, mixtures thereof and the like. The catalysts can be employed in quantities of from about 0.5 to about 20, preferably from about 2 to about 5, weight percent based upon the total weight of the reactants. The reaction can be conducted in the absence of a catalyst but the reaction time is typically increased.

The condensation reaction is conducted in an atmosphere exclusive of oxygen, preferably with removal of water generated by the reaction. An inert atmosphere such as nitrogen, xenon, argon, etc. is appropriate.

The condensation reaction is usually conducted at a temperature of from about 130° C. to about 230° C., preferably from about 140° C. to about 190° C. for from about 0.5 to about 24 hours (1800 s to 86,400 s), preferably from about 1 to about 8 hours (3600 s to 28,800 s).

The reactants are usually employed in quantities which provide a mole ratio of substituted pyridine and/or substituted pyrazine to substituted aromatic aldehyde of from about 0.33:1 to about 6:1, preferably from about 1:1 to about 3:1.

Suitable substituted pyridines which can be employed include, for example, 2,3-dimethyl pyridine, 2,4-dimethyl pyridine, 2,5-dimethyl pyridine, 2,6-dimethyl pyridine, 3,4-dimethyl pyridine, 3,5-dimethyl pyridine, 3,5-dimethyl-2-ethyl pyridine, 2,3,4,6-tetramethyl pyridine, 2,3,5-trimethyl pyridine, 2,3,6-trimethyl pyridine, 2,4,5-trimethyl pyridine, 2,4,6-trimethyl pyridine, 2,4-dimethyl-6-hydroxy pyridine, 2,6-dimethyl-4-hydroxy pyridine, 2,6-dimethyl-3-hydroxy pyridine, 2,4,6-trimethyl-5-hydroxy pyridine, mixtures thereof and the like.

Suitable substituted pyrazines which can be employed include, for example, 2,5-dimethyl pyrazine, 2,3-dimethyl pyrazine, 2,6-dimethyl pyrazine, 2,3,5-trimethyl pyrazine, 2,3,5,6-tetramethyl pyrazine, 2,5-dimethyl-6-hydroxyl pyrazine, 2,5-dimethyl-3-ethyl pyrazine, mixtures thereof and the like.

Suitable substituted aromatic aldehydes which can be employed herein include, for example, 2-hydroxy benzaldehyde, 3-hydroxy benzaldehyde, 4-hydroxy benzaldehyde, 2-hydroxy-3-methyl benzaldehyde, 2-hydroxy-3-ethyl benzaldehyde, 4-hydroxy-3,5-dimethyl benzaldehyde, terephthaldehyde, 2,6-dihydroxy benzaldehyde, methyl terephthaldehydes, dimethyl terephthaldehydes, ethyl terephthaldehydes, mixtures thereof and the like.

Several hydroxy styryl pyridine precursors have been described by Chiang and Hartung in *J. Org. Chem.*, Vol. 10, pp. 21–25 (1945); by Bramsch in *Chemische Berichte*, Vol. 42, pp. 1193–1197 (1909); Franke in *Chemische Berichte*, Vol. 38, pp. 3724–3728 (1905) and Yan, et. al. in *Org. Coatings and Applied Poly. Sc. Proc.*, Vol. 46, pp. 482–488 (1982) published by the American Chemical Society. The corresponding hydroxy styryl pyrazine precursors may be prepared using the above described methods wherein the appropriate substituted pyrazine is used in place of the substituted pyridine.

A monomeric hydroxy styryl pyridine and/or pyrazine precursor can be oligomerized (prepolymerized) typically by heating at a temperature of about 180° C. to about 300° C. for from about 0.5 to about 8 hours (1800 s to 28,800 s). Polymerization is completed at a temperature of from about 250° C. to about 300° C. for an additional 1 to about 10 hours (3600 s to 36,000 s). The hydroxyl styryl pyridine and/or pyrazine products obtained by the aforementioned condensation reaction can be fractionated to provide monomeric and oligomeric precursors employing methods well known to the skilled artisan. Such methods include, for example, preparative gel permeation chromatography, solvent fractionation or extraction and recrystallization.

The cyanation reaction is accomplished with a suitable cyanogen halide wherein the hydroxyl containing styryl pyridine and/or pyrazine precursor material is reacted with a stoichiometric or slight excess of stoichiometric quantity of a cyanogen halide and a stoichiometric quantity of a base material per hydroxyl group contained in the precursor material.

If desired, the hydroxyl styryl pyridine and/or pyrazine precursor materials can be reacted with less than stoichiometric quantities of cyanogen halide and less than stoichiometric quantities of a base per hydroxyl group. This provides a styryl pyridine and/or pyrazine with unreacted hydroxyl groups. Although this composition is less preferred, it is still a useful composition of the present invention.

Suitable cyanogen halides include, for example, cyanogen bromide, cyanogen chloride or a mixture thereof. Alternately, the method of Martin and Bauer described in *Org. Synthesis*, Vol. 61, pp. 35–68 (1983) published by John Wiley and Sons which is incorporated herein by reference can be employed to generate the cyanogen halide in situ from an alkali metal cyanide, such as sodium cyanide and a halogen such as chlorine or bromine.

Suitable base materials include both inorganic and tertiary amines such as sodium hydroxide, potassium hydroxide, triethylamine, mixtures thereof and the like. A particularly suitable base is triethylamine.

If desired, the reaction can be conducted in the presence of a solvent such as, for example, water, ketones, chlorinated hydrocarbons, mixtures thereof and the like. Particularly suitable solvents include, for example, methylene chloride and acetone.

The cyanation reaction is usually conducted at temperatures of from about −40° C. to about 60° C., preferably from about −10° C. to about 10° C.

The styryl pyridine cyanate and styryl pyrazine cyanate compositions of the present invention can be cured (homopolymerized) by heating from 70° to 350° C. or more, preferably by heating from 150° to 250° C. A suitable catalyst may be used at a concentration of 0.001 to about 2 percent by weight. Operable catalysts include those taught by U.S. Pat. No. 4,094,852. Most preferred catalysts are cobalt naphthenate and cobalt octoate. Prepolymerization (B-staging or oligomerization) may be affected by using lower cure temperatures and/or shorter curing times. Curing of the prepolymerized resin may then be completed at a later time or immediately following prepolymerization to comprise a single curing step.

Styryl pyridine prepolymers and/or polystyryl pyridines which can be employed herein include those described by Ropars et al in U.S. Pat. No. 3,994,862 and by Malassine et al in U.S. Pat. No. 4,163,740 which are incorporated herein by reference.

Suitable vinyl styryl pyridines and/or vinyl polystyryl pyridines which can be employed herein include those described by Ratto et al in U.S. Pat. No. 4,362,860, by Ming-ta, et. al. in *Technology Vectors*, Vol. 29, pages 1034–1042 (1984) published by the Society for the Advancement of Material and Process Engineering which are incorporated herein by reference. A specific preparation of a vinyl polystyryl pyridine follows:

PREPARATION 1

Vinylpolystyryl Pyridine Prepared Using 2,4,6-Trimethyl Pyridine, Terephthalaldehyde and 2-Methyl-5-Vinyl Pyridine Terephthalaldehyde (603 grams, 4.5 moles), 2,4,6-trimethyl pyridine (363 grams, 3.0 moles) and acetic acid (540 grams, 9.0 moles) were added to a 4-liter glass resin kettle equipped with a mechanical stirrer, thermometer, nitrogen inlet, and condensor. The combined reactants were maintained under a nitrogen atmosphere with stirring then 5 minutes (300 s) later acetic anhydride (918 grams, 9.0 moles) was added. The reaction mixture was heated to 140° C. and allowed to reflux. After 7 hours (25,200 s) of reaction at the 140° C. temperature, the reaction mixture was cooled to 100° C. and 2-methyl-5-vinyl pyridine (536 grams, 4.5 moles) was added. The reaction mixture was reheated to 120° C. and maintained for an additional 7 hours (25,200 s). At that time, the reaction product was cooled to 100° C. and neutralized with 10 percent aqueous sodium hydroxide. The aqueous layer was decanted and the resulting mustard colored product was multiply washed with deionized water. The washed product was dissolved to form a 10 percent by weight solution in tetrahydrofuran and this solution was filtered. The filtrate was poured over ice and allowed to stand for five minutes (300 s). The precipitated product was recovered by adding the product-ice slurry to a large excess of deionized water followed by filtering. The solid, powdery product was recovered in the filter and again water washed, followed by drying under vacuum (30 inches, 762 mm, Hg) at 75° C. Gel permeation chromatographic analysis using polystyrene standards demonstrated a weight average molecular weight of 2500 (polystyrene equivalent).

Suitable alkenyl phenyl cyanates which can be employed herein include, for example, those represented by the formula

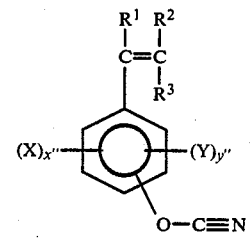

wherein each $R^1$, $R^2$ and $R^2$ is independently hydrogen or a hydrocarbyl group having from 1 to about 3 carbon atoms; each X is independently hydrogen, a hydrocarbyl or hydrocarbyloxy group having from 1 to about 4 carbon atoms, chlorine or bromine or a phenyl group; each Y is independently hydrogen or a hydrocarbyl group having from 1 to about 4 carbon atoms and $x''$ and $y''$ are positive integers and the sum of $x''$ plus $y''$ is 4.

Particularly suitable alkenyl phenyl cyanates include, for example, p-isopropenylphenyl cyanate, p-vinylphenyl cyanate, m-vinylphenyl cyanate, methyl-p-isopropenylphenyl cyanate, 3-chloro-4-isopropenylphenyl cyanate and the like. It is most preferred that the alkenyl phenyl cyanate be substantially free of dimeric and/or oligomeric components although it is operable to use an alkenyl phenyl cyanate containing substantial (up to 90 percent by weight) dimeric and/or oligomeric components. Said components are formed during the cyanation reaction of an alkenylphenol containing the corresponding dimeric diphenols and/or oligomeric polyphenols. A specific preparation of p-isopropenylphenyl cyanate follows:

PREPARATION 2

Synthesis of p-Isopropenylphenyl Cyanate

A 201.26 gram (1.50 mole) portion of p-isopropenyl phenol, 166.84 grams (1.575 moles) of cyanogen bromide and 900 milliliters of acetone were added to a reactor and maintained under a nitrogen atmosphere with stirring. The p-isopropenyl phenol used herein was of in excess of 99 percent purity. The stirred solution was cooled to −5° C. then 151.79 grams (1.50 mole) of triethylamine was added to the reactor over a twenty minute (1200 s) period and so as to maintain the reaction temperature at −5° to 0° C. After completion of the triethylamine addition, the reactor was maintained at −3° to 5° C. for an additional thirty-two minutes (1820 s), followed by addition of the reactor contents to 1 gallon of chilled deionized water. After five minutes (300 s) the water and product mixture was multiply extracted with three 400 milliliter volumes of methylene chloride. The combined methylene chloride extract was washed with 500 milliliters of 5 percent aqueous hydrochloric acid followed by washing with 800 milliliters of deionized water then drying over anhydrous sodium sulfate. The dry methylene chloride extract was filtered and solvent removed by rotary evaporation under vacuum. p-Isopropenylphenyl cyanate (207.24 grams) was recovered in 86.8 percent yield as a transparent, light amber colored liquid. Infrared spectrophotometric analysis of a film sample of the product confirmed the product structure (disappearance of phenolic hydroxyl group, appearance of —C≡N group). Gas chromatographic-mass spectroscopic analysis of the produuct confirmed the structure of p-isopropenylphenyl cyanate (parent ion m/e=159) with essentially no other compounds being present.

Suitable aromatic dicyanates (polycyanates) which can be employed herein include, for example, those represented by the formulas

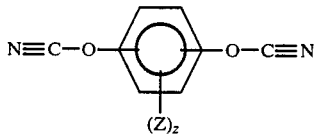
(V)

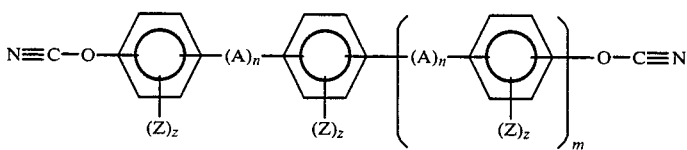
(VI)

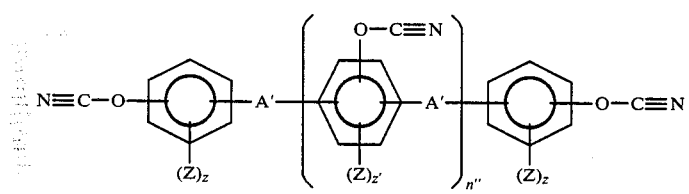
(VII)

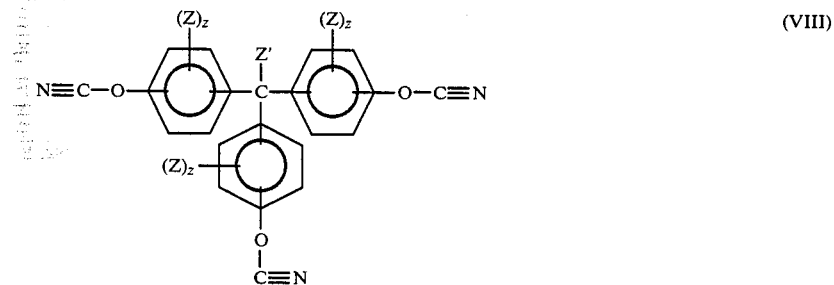
(VIII)

wherein each A is independently an alkylene group having from 1 to about 10 carbon atoms, preferably from 1 to about 4 carbon atoms,

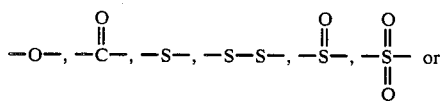 or

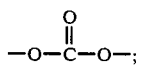

each A' is independently an alkylene group having from 1 to about 6, preferably from 1 to about 4 carbon atoms or

each Z is independently hydrogen, a hydrocarbyl or hydrocarbyloxy group having from 1 to about 10, preferably 1 to about 4 carbon atoms, a halogen, preferably chlorine or bromine, a phenyl group, or a —O—C≡N group; Z' is independently hydrogen, a hydrocarbyl or hydrocarbyloxy group having from 1 to about 10, preferably 1 to about 4 carbon atoms, a halogen, preferably chlorine or bromine, or a phenyl group; p has a value of from zero to about 10, preferably from zero to 3; n has a value of zero or 1; m has a value from zero to about 100, preferably from zero to about 30; n" has a value of from about 0.001 to about 6, preferably from about 0.01 to about 3; z has a value of 4, and z' has a value of 3.

Particularly suitable aromatic dicyanates (polycyanates) which can be employed herein include bisphenol A dicyanate; the dicyanates of 4,4'-dihydroxydiphenyl oxide, resorcinol, 4,4'-thiodiphenol, 4,4'-sulfonydiphenol, 3,3',5,5'-tetrabromobisphenol A, 2,2',6,6'-tetrabromobisphenol A, 3-phenylbisphenol A, 4,4'-dihydroxybiphenyl, 2,2'-dihydroxybiphenyl, 2,2',4,4'-tetrahydroxydiphenyl methane, 2,2',6,6'-tetramethyl-3,3',5,5'-tetrabromobisphenol A, 5,5'-dimethoxybisphenol A;

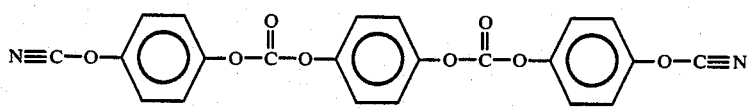

the tricyanate of tris(hydroxyphenyl)methane, the polycyanate of a phenolformaldehyde condensation product (novolac), the polycyanate of a dicyclopentadiene and phenol condensation product and the like. The aromatic polycyanates may be used either alone or in any combination. A specific preparation of bisphenol A dicyanate follows:

PREPARATION 3

Synthesis of Bisphenol A Dicyanate

A 342.45 gram portion of 4,4'-isopropylidene diphenol (1.50 moles), 333.68 grams (3.15 moles) of cyanogen bromide and 1000 milliliters of acetone were added to a reactor and maintained under a nitrogen atomsphere with stirring. The stirred solution was cooled to −5° C. then 305.09 grams of triethylamine (3.015 moles) was added to the reactor over a twenty-five minute (1500 s) period and so as to maintain the reaction temperature at −5° to 0° C. After completion of the triethylamine addition, the reactor was maintained at −5° to 5° C. for an additional fifty minutes (3000 s), followed by addition of the reactor contents to 1 gallon of chilled deionized water. After five minutes (300 s) the water and product mixture was multiply extracted with three 500 milliliter volumes of methylene chloride. The combined methylene chloride extract was washed with 500 milliliters of 5 percent aqueous hydrochloric acid followed by washing with 800 milliliters of deionized water then drying with anhydrous sodium sulfate. The dry methylene chloride extract was filtered and solvent removed by rotary evaporation under vacuum. Bisphenol A dicyanate (360.74 grams) was recovered in 86.4 percent yield as a light tan crystalline solid. Infrared spectrophotometric analysis of a film sample of the product confirmed the product structure (disappearance of phenolic hydroxyl group, appearance of —C≡N group).

Suitable bismaleimides (polymaleimides) which can be employed herein include, for example, those represented by the formulas

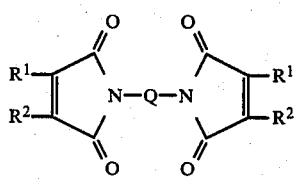

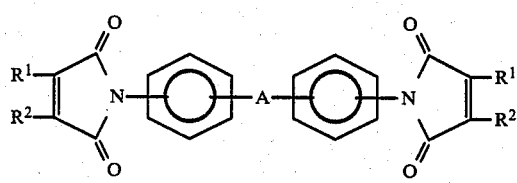

-continued

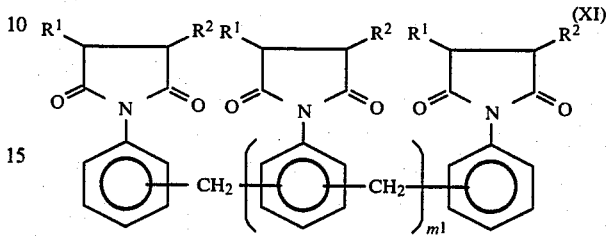

wherein $R^1$, $R^2$ and A are as hereinbefore defined; Q is an alkylene group having from 2 to about 12 carbon atoms and $m^1$ has a value of 0.01 to about 10.

Particularly suitable bismaleimides (polymaleimides) which can be employed herein include, for example, N,N'-ethylenebismaleimide, N,N'-ethylenebis(2-methyl-maleimide), N,N'-hexamethylenebismaleimide, N,N'-(oxydi-p-phenylene)bismaleimide, N,N'-(methylenedi-p-phenylene)-bismaleimide, N,N'-(methylenedi-p-phenylene)bis(2-methylmaleimide), N,N'-(thiodi-p-phenylene)bismaleimide, N,N'-(sulfonyldi-m-phenylene)bismaleimide, N,N'-(isopropylidenedi-p-phenylene)bismaleimide, polymethylene polyphenylene polymaleimides and the like. The bismaleimides (polymaleimides) may be used either alone or in any combination.

The bismaleimides (polymaleimides) can be prepared by reacting a stoichiometric quantity of a maleic anhydride per amine group with a diamine (polyamine) in the presence of a suitable solvent.

Preparation of bismaleimides (polymaleimides) is disclosed by Arnold, et al in U.S. Pat. No. 2,462,835 and by Searle in U.S. Pat. No. 2,444,536 which are incorporated herein by reference. A specific preparation of N,N'-(methylenedi-p-phenylene)bismaleimide follows:

PREPARATION 4

Synthesis of N,N'-(methylenedi-p-phenylene)bismaleimide

A 106.0 gram (1.08 moles) portion of maleic anhydride and 400 milliliters of N,N-dimethylformamide were added to a reactor and maintained under a nitrogen atmosphere with stirring. The stirred solution was cooled to 5° C. then 107.0 grams (0.54 mole) of methylenedianiline dissolved in 200 milliliters of N,N-dimethylformamide was added to the reactor over a sixty minute (3600 s) period and so as to maintain the reaction temperature at 5° to 10° C. After completion of the methylenedianiline in N,N-dimethylformamide solution addition the reactor was maintained at 5° to 10° C. for an additional 120 minutes (7200 s). The reactor was then allowed to warm to room temperature (25° C.), and the reaction product was removed and rotary evaporated at 55° to 60° C. under vacuum. After approximately 300 milliliters of N,N-dimethylformamide and water had distilled off, a voluminous light yellow colored precipitate formed and was recovered by filtration. The recovered precipitate was recrystallized from acetone and then dried in a vacuum oven at 80° C. N,N'- methylenedi-p-phenylene)bismaleimide (172.6 grams) was recovered in 89.2 percent yield as a light yellow colored powder. Infrared spectrophotometric analysis of a potassium chloride pellet of the product confirmed the product structure. Nuclear magnetic resonance spectroscopy provided further confirmation of the product structure.

Suitable epoxy resins include materials having an average of more than one vicinal epoxide group per molecule such as, for example, the glycidyl ethers represented by the formulas drin and a basic acting material. Said reaction generally involves two distinct steps: coupling reaction of the epihalohydrin and diphenol or polyphenol to provide a halohydrin intermediate and dehydrohalogenation reaction of the halohydrin intermediate to provide the glycidyl ether product. Suitable catalysts and reaction conditions for preparing polyepoxides are described in the *Handbook of Epoxy Resins* by Lee and Neville, McGraw-Hill (1967) which is incorporated herein by reference.

Particularly preferred epoxy resins include, for example, styryl pyridine epoxy resins described by Yan, et. al. in "Styryl-Pyridine Based Epoxy Resins: Synthesis and Characterization" in *Organic Coatings* and Applied Polymer Science Proceedings, Vol. 46, pp. 482–488 (1982) published by American Chemical Society which is incorporated herein by reference.

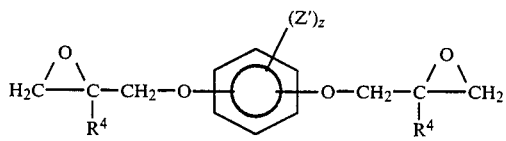

XII.

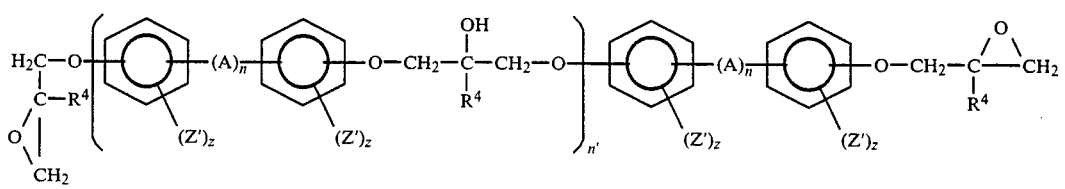

XIII.

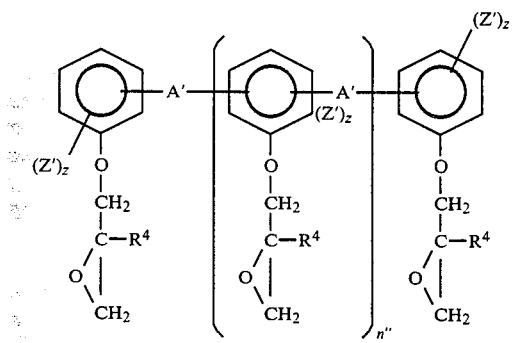

XIV.

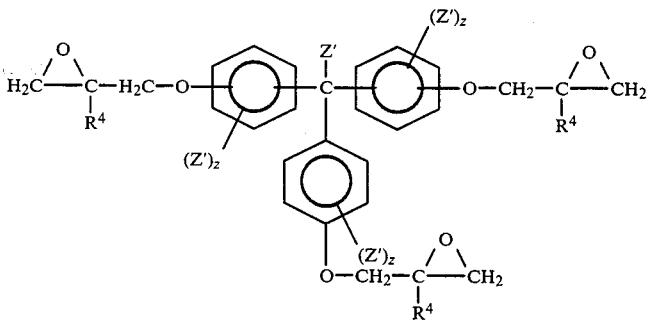

XV.

wherein A, A', Z', n, n", z, z' and p are as hereinbefore defined; each $R^4$ is independently hydrogen or a hydrocarbyl group having from 1 to about 4 carbon atoms; and n' has a value of from about zero to about 30, preferably from about zero to about 5.

Particularly suitable polyepoxides which can be employed herein include, for example, the diglycidyl ethers of resorcinol, bisphenol A, 3,3',5,5'-tetrabromobisphenol A, the triglycidyl ether of tris(hydroxyphenyl)methane, the polyglycidyl ether of a phenol-formaldehyde condensation product (novolac), the polyglycidyl ether of dicyclopentadiene and phenol condensation product and the like. The polyepoxides can be used either alone or in combination.

The aforementioned epoxy resins can be prepared by reaction of a diphenol or polyphenol with an epihalohy- Suitable alkenylphenol capped styryl pyridines and/or alkenylphenol capped polystyryl pyridines which can be employed herein include those prepared by reacting a di or polymethyl pyridine compound with an aromatic di or polyaldehyde. The resultant product is then reacted with an alkenyl phenol represented by the formula

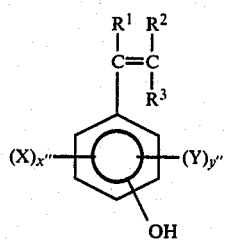

(XVI)

wherein $R^1$, $R^2$, $R^3$, X, Y, x" and y" are as hereinbefore defined. Preparation of said alkenylphenol capped styryl pyridines and/or alkenylphenol capped polystyryl pyridines is taught by LaTulip in pending application Ser. No. 609,156 filed May 11, 1984 which is incorporated herein by reference.

The styryl pyridine cyanate and/or styryl pyrazine cyanate copolymers can be prepared in similar manner to the preparation of homopolymers of styryl pyridine cyanates and/or styryl pyrazine cyanates.

Among other uses, the compositions of the present invention are especially useful in the preparation of high temperature resistant composites or laminates with carbon fibers, glass fibers, milled carbon fibers, metal fibers, metal powders, glass fiber woven mat, carbon fiber woven mat, graphite fibers, aramid fibers, asbestos fibers, carbon powders, graphite powders, mixtures thereof and the like. If desired, other materials can be employed such as, for example, fillers, pigments, dyes, other additives and the like.

The compositions of the present invention are also useful in coatings, cast parts, moldings and the like and are especially useful in high temperature environments.

The following examples are illustrative of the present invention but are not to be construed as to limiting the scope thereof in any manner.

EXAMPLE 1

A. Preparation of Hydroxy Functional Styryl Pyridine From 2,4,6-Trimethyl Pyridine and 4-Hydroxy Benzaldehyde In a 500-ml glass resin kettle, equipped with a stirrer, thermometer, nitrogen purge and reflux condenser, there was introduced 378.9 grams (3.11 moles) of 4-hydroxy benzaldehyde and 187.9 grams (1.55 moles) of 2,4,6-trimethyl pyridine. The reaction mixture was heated and agitated until a homogenous mixture resulted. Then, 6.32 ml of concentrated sulfuric acid was added (equivalent to 2.0 weight % of total reactants). This mixture was reacted for four hours (14,400 s) over a temperature range of 165° C. to 195° C. The resulting product was a viscous, maroon-colored liquid. The reaction product was an oligomeric mixture based on bis(4-hydroxy styryl) methyl pyridine. When allowed to cool to ambient temperature, a very hard and brittle solid formed. The properties of the product were Melting Point Range=115° C. to 130° C.

Elemental Weight % Analysis=75.9% carbon, 4.0% nitrogen, 5.6% hydrogen.

IR Spectrum Analysis: The product totally lacked the aldehyde peak (1670 cm$^{-1}$), thus indicating that the hydroxy benzaldehyde was totally reacted. As expected, trans-unsaturation absorbance bands were found to be present (970 cm$^{-1}$). Aromatic carbon-oxygen bonds were also determined to exist (1250 cm$^{-1}$) due to the phenolic groups. Phenolic hydroxyl group absorbance (3300 cm$^{-1}$) was also observed.

B. Preparation of Styryl Pyridine Cyanate

A portion of the reaction product of a 1 to 2 mole ratio of 2,4,6-trimethyl pyridine and p-hydroxy benzaldehyde (7.30 grams, 0.0443 moles of hydroxyl groups) from 1-A above and acetone (150 grams) were added to a 1-liter glass resin kettle and maintained under a nitrogen atmosphere. Stirring and cooling were both started and when the temperature of the slurry reached 0° C., cyanogen bromide was added (4.93 grams, 0.0466 mole). After five minutes (300 s), triethylamine (4.51 grams, 0.0466 mole) was added dropwise over a four minute (240 s) period and so as to maintain the reaction temperature between 0° and 4° C. The reaction was allowed to progress for an additional 30 minutes (1800 s) between reaction temperatures of −1° to 5° C. After this time, the reaction slurry was filtered. The recovered filtrate was added to 750 milliliters of deionized water producing a voluminous pale white colored precipitate. The precipitate was recovered by filtration, washed with 100 milliliters of deionized water and then dried under vacuum at 25° C. to a constant weight of 2.2 grams. The unreacted trimethyl pyridine and p-hydroxy benzaldehyde adduct as well as triethylamine hydrochloride were recovered from the filter (5.2 grams), as a pale white colored powder. Infrared spectrophotometric analysis of a potassium bromide pellet of the product revealed the presence of cyanate group absorbance (2225 cm$^{-1}$ and 2260 cm$^{-1}$) accompanied by a substantial absence of a hydroxy group absorbance (3300 cm$^{-1}$). As expected, trans-unsaturation absorbance (970 cm$^{-1}$) and aromatic carbon-oxygen absorbance (1250 cm$^{-1}$) remained.

EXAMPLE 2

Copolymerization of a Styryl Pyridine Cyanate and a Polyepoxide

A 0.190 gram (0.0005 mole) portion of the styryl pyridine cyanate from Example 1-B, 0.183 gram (0.0005 mole) of a diglycidyl ether of bisphenol A having an epoxide equivalent weight (EEW) of 183 and 1.5 grams of methylene chloride were combined to form a solution. This solution was used to cast a film on an aluminum plate. After drying, the film and plate were placed in a vented, forced-air, convection-type oven and cured at 200° C. for 2.0 hours (7200 s). After this time, the cured copolymer was recovered as a transparent, light amber colored film.

Thermogravimetric analysis (TGA) of a 6.97 milligram portion of the film was performed. Weight loss was recorded as a function of temperature at a 10° C. per minute (0.167° C./s) rate of increase in a stream of nitrogen flowing at 35 cubic centimeters per minute (0.583 cc/s). The results are reported in Table I.

TABLE I

| Weight Loss (%) | | | | | |
|---|---|---|---|---|---|
| 100° C. | 300° C. | 350° C. | 400° C. | 500° C. | 950° C. |
| 0.1 | 1.1 | 5.0 | 25.2 | 52.6 | 65.6 |

Differential scanning calorimetry (DSC) of a 11.50 milligram portion of the film was performed. The sample was loaded and run in a nitrogen atmosphere at a scan rate of 10° C. per minute (0.167° C./s) from 30° C.

to 450° C. The DSC revealed a lack of a glass transition temperature (Tg).

EXAMPLE 3

A. Hydroxy Functional Styryl Pyridine Prepared From 2,4,6-Trimethyl Pyridine, 2,6-Dimethyl Pyridine and 4-Hydroxy Benzaldehyde 2,4,6-trimethyl pyridine (588.0 grams, 4.85 moles) and zinc chloride catalyst (26.0 grams) were added to a reactor and heated with stirring under a nitrogen atmosphere to a reflux. The reaction mixture was cooled to 150° C. then p-hydroxy benzaldehyde (887.0 grams, 7.26 moles) was added in 100 to 150 gram aliquots over a 110 minute (6600 s) period and so as to maintain the reaction temperature between 145° to 154° C. After addition of the p-hydroxy benzaldehyde was complete, the reaction temperature was increased to 160° C. After 4 hours (14400 s) of reaction at the 160° C. temperature, 2,6-dimethylpyridine (560.0 grams, 5.23 moles) was added to the reactor, then collection of a methyl pyridines—water azeotrope into a Dean Stark trap—cold water condenser assembly began. After 150 milliliters of azeotrope was collected, 150 milliliters of fresh 2,6-dimethylpyridine was added to the reaction mixture. The reaction was allowed to progress for an additional 4 hours (14400 s) at the 160° C. reaction temperature followed by cooling to room temperature. After this time, the final reaction stoichiometry was a 1 to 1.5 to 1 mole ratio of 2,4,6-trimethyl pyridine to p-hydroxy benzaldehyde to 2,6-dimethylpyridine.

Portions of the hydroxy styryl pyridine product were worked up as needed by vigorously mixing the dark caramel colored viscous reaction product from above with an excess of methylene chloride. This provided a methylene chloride insoluble light orange colored powder which was recovered by filtration. The powder was multiply washed with an excess of boiling water and then dried under vacuum at 100° C. to a constant weight. Infrared spectrophotometric analysis demonstrated a lack of aldehyde absorbance (1670 cm$^{-1}$), thus indicating that the hydroxy benzaldehyde was totally reacted. As expected, trans-unsaturation absorbance was found to be present (970 cm$^{-1}$). Aromatic carbon-oxygen absorbance (1250 cm$^{-1}$) and phenolic hydroxyl group absorbance (3300 cm$^{-1}$) confirmed the presence of the phenolic groups. Titration demonstrated the presence of 8.04 percent by weight phenolic hydroxyl groups. The product had a melting point range of 160° to 170° C.

B. Preparation of Styryl Pyridine Cyanate Using Excess Cyanogen Bromide Stoichiometry A portion of the reaction product of a 1 to 1.5 to 1 mole ratio of 2,4,6-trimethyl pyridine to p-hydroxy benzaldehyde to 2,6-dimethylpyridine (100.0 grams, 0.473 mole of hydroxyl groups) from 3-A above and acetone (750 milliliters) were added to a 2-liter glass resin kettle and maintained under a nitrogen atmosphere. Stirring was started and allowed to progress for 40 minutes (2400 s) then cooling of the reactor commenced. When the reaction temperature reached −5° C., cyanogen bromide (105.67 grams, 0.9975 mole) was added. After five minutes (300 s), triethylamine (96.64 grams, 0.955 mole) was added dropwise over a 20 minute (1200 s) period and so as to maintain the reaction temperature between −5° and 0° C. The reaction was allowed to progress for an additional 45 minutes (2700 s) between reaction temperatures of −5° to 5° C. After this time, the reaction slurry was filtered. The recovered filtrate was added to 1 gallon (3.79 l) of deionized water producing an amber oil precipitate. The oil product was recovered by extraction with three 500 milliliter portions of methylene chloride. The combined methylene chloride extract was washed with 1500 milliliters of deionized water, dried over anhydrous sodium sulfate and then filtered. The dry methylene chloride solution was rotary evaporated under vacuum to a constant weight of 118.6 grams. Infrared spectrophotometric analysis of a film sample of the amber colored, viscous oil product confirmed the product structure for the styryl pyridine cyanate (presence of cyanate group absorbance accompanied by total absence of hydroxyl group absorbance, retention of trans-unsaturation absorbance and aromatic carbon-oxygen absorbance).

EXAMPLE 4

Use of a Styryl Pyridine Cyanate in a Cured Glass Laminate

A 50.0 gram portion of the styryl pyridine cyanate from Example 3-B, 150 grams of methylene chloride and 0.100 gram of cobalt naphthenate (6.0 percent active) were combined to form a solution. A set of three 12-inch by 12-inch (304.8 mm × 304.8 mm) woven fiberglass cloth pieces were then equally impregnated with the solution. The fiberglass cloth used was a commercial-grade product treated with a proprietary coupling agent (Burlington 76-28 electrical laminating cloth) and had an average weight of 0.14 gram per square inch (0.0217 g/cm$^2$). The set of impregnated cloths were allowed to dry for 1 hour (3600 s) at room temperature (25° C.) followed by additional drying and B-staging in a vented, forced-air, convection-type oven for 10 minutes (600 s) at 100° C. Each cloth was cooled and found to be tack-free at room temperature and then cut to provide ten 6-inch by 6-inch (152.4 mm by 152.4 mm) pieces which were loaded into a stainless steel frame and placed between stainless steel plates which had been treated with a silicone mold release. The plates were loaded into a 200° C. hot press (Pasadena Hydraulics, Inc., Model P-215) and maintained for two hours (7200 s) at 5000 psi (34.5 MPa). After this time a 6-inch by 6-inch by 1/16-inch (152.4 mm by 152.4 mm by 1.5785 mm) non-transparent, dark amber colored, rigid laminate was recovered and cut to provide a set of six 1-inch by 2-inch by 1/16-inch (25.4 mm by 50.8 mm by 1.5875 mm) flexural strength test pieces. The flexural strength test pieces were post-cured at 200° C. for two hours (7200 s) and then tested on an Instron machine with standard methods (ASTM D-790). The Instron machine was set at a 1-inch (25.4 mm) span, 0.02 inch (0.0085 mm/s) crosshead speed and a 0.5 inch per minute (0.21166 mm/s) chart speed. The Barcol hardness value is on the 934-1 scale. The results are reported in Table II.

TABLE II

| Barcol Hardness | 44 |
|---|---|
| Flexural Strength, psi/kPa | 36,402/250985 |
| Flexural Modulus, psi/kPa | 2,246,000/15485721 |

EXAMPLE 5

Thermogravimetric Analysis (TGA) of a Homopolymerized (Cured) Styryl Pyridine Cyanate A portion (1.0 gram) of the resin solution prepared in Example 4 for the impregnation of fiberglass cloths was devolatilized to remove methylene chloride solvent then cured for two hours (7200 s) at 200° C. and post-cured two hours (7200 s) at 200° C. Thermogravimetric analysis (TGA) of a 8.91 milligram portion of the resin was performed. Weight loss was recorded as a function of temperature at a 10° C. per minute (0.167° C./s) rate of increase in a stream of nitrogen flowing at 35 cubic centimeters per minute (0.583 cc/s). The results are reported in Table III.

TABLE III

| Weight Loss (%) | | | | | | |
|---|---|---|---|---|---|---|
| 100° C. | 300° C. | 350° C. | 400° C. | 500° C. | 700° C. | 950° C. |
| 0.0 | 5.0 | 11.6 | 20.2 | 34.0 | 43.0 | 47.5 |

EXAMPLE 6

Use of a Styryl Pyridine Cyanate, p-Isopropenylphenyl Cyanate and Bisphenol A Dicyanate Solution to Prepare a Cured Fiberglass Laminate A 14.24 gram portion of the styryl pyridine cyanate from Example 3-B, 7.96 grams of p-isopropenylphenyl cyanate from Preparation 2, 27.8 grams of bisphenol A dicyanate from Preparation 3, 150 grams of methylene chloride and 0.10 gram of cobalt naphthenate (6.0 percent active) were combined to form a solution. A set of three 12 inch by 12 inch (304.8 mm by 304.8 mm) woven fiberglass cloth pieces were then equally impregnated with the solution. The fiberglass cloth used was a commercial-grade product treated with a proprietary coupling agent (Burlington 76-28 electrical laminating cloth) and had an average weight of 0.14 gram per square inch (0.0217 g/cm²). The set of impregnated cloths were allowed to dry for one hour (3600 s) at room temperature (25° C.) followed by B-staging in a vented, forced-air, convection-type oven for 10 minutes (600 s) at 100° C. Each cloth was cooled and found to be tack-free at room temperature and then cut to provide ten 6 inch by 6 inch (152.4 mm by 152.4 mm) pieces. The pieces were stacked into a 6 inch by 6 inch by 1/16 inch (152.4 mm by 152.4 mm by 1.5875 mm) stainless steel frame and placed between stainless steel plates which had been treated with a silicone mold release. The plates were loaded into a 200° C. hot press (Pasadena Hydraulics, Inc., Model P-215) and maintained for two hours (7200 s) at 5000 psi (34.5 MPa). After this time, a 6 inch by 6 inch by 1/16 inch (152.4 mm by 152.4 mm by 1.5875 mm) amber-colored, semi-transparent, rigid laminate was recovered and cut to provide a set of six 1 inch by 2 inch by 1/16 inch (25.4 mm by 50.8 mm by 1.5875 mm) flexural strength test pieces. The flexural strength test pieces were post-cured at 200° C. for two hours (7200 s) and then tested on an Instron machine with standard methods (ASTM D-790). The Instron machine was set at a 1 inch (25.4 mm) span, 0.02 inch per minute (0.0085 mm/s) crosshead speed and a 0.5 inch per minute (0.21166 mm/s) chart speed. The Barcol hardness value is on the 934-1 scale. The results are reported in Table IV.

TABLE IV

| | |
|---|---|
| Barcol Hardness | 72 |
| Flexural Strength, psi/kPa | 73,771/508,636 |
| Flexural Modulus, psi/kPa | 3,467,000/23,904,272 |

EXAMPLE 7

Thermogravimetric Analysis (TGA) of a Styryl Pyridine Cyanate, a Polycyanate and an Alkenylphenyl Cyanate Copolymer A 1.0 gram portion of the styryl pyridine cyanate, bisphenol A dicyanate, p-isopropenylphenyl cyanate, cobalt naphthenate and methylene chloride solution from Example 6 was used to cast a film on an aluminum plate. After drying, the film and plate were placed in a vented, forced-air, convection-type oven and cured at 200° C. for 4.0 hours (14,400 s). After this time, the cured copolymer was recovered as a transparent amber-colored film.

Thermogravimetric analysis (TGA) of a 17.10 milligram portion of the film was performed. Weight loss was recorded as a function of temperature at a 10° C. per minute (0.167° C./s) rate of increase in a stream of nitrogen flowing at 35 cubic centimeters per minute (0.583 cc/s). The results are reported in Table V.

TABLE V

| Weight Loss (%) | | | | | |
|---|---|---|---|---|---|
| 100° C. | 300° C. | 350° C. | 400° C. | 500° C. | 950° C. |
| 0 | 2.5 | 10.4 | 36.0 | 55.2 | 64.8 |

EXAMPLE 8

Differential Scanning Calorimetry (DSC) of a Styryl Pyridine Cyanate, a Polycyanate and an Alkenylphenyl Cyanate Copolymer A 8.00 milligram portion of the cured resin from Example 7 was analyzed by differential scanning calorimetry (DSC) under a nitrogen atmosphere flowing at 35 cubic centimeters per minute (0.583 cc/s) and at a scanning rate of 10° C. per minute (0.167° C./s) from 30° to 320° C. The midpoint glass transition temperature (Tg) was 171.0° C.

EXAMPLE 9

Thermogravimetric Analysis (TGA) of a Thermally Cured Styryl Pyridine Cyanate A 1.0 gram portion of the styryl pyridine cyanate from Example 3-B was cured for 2 hours (7200 s) at 200° C. Thermogravimetric analysis (TGA) of a 10.18 milligram portion of the cured product was performed. Weight loss was recorded as a function of temperature at a 10° C. per minute (0.167° C./s) rate of increase in a stream of nitrogen flowing at 35 cubic centimeters per minute (0.583 cc/s). The results are reported in Table VI.

TABLE VI

| Weight Loss | | | | | | |
|---|---|---|---|---|---|---|
| 100° C. | 300° C. | 350° C. | 400° C. | 500° C. | 700° C. | 950° C. |
| 0 | 4.1 | 9.6 | 15.9 | 31.2 | 41.0 | 43.2 |

COMPARATIVE EXPERIMENT A

Thermogravimetric Analysis (TGA) of a Thermally Cured Hydroxy Styryl Pyridine A 1.0 gram portion of the hydroxy styryl pyridine from Example 3-A (and used in the preparation of the styryl pyridine cyanate of Example 3-B) was cured for 18 minutes (1080 s) at 185° C., 85 minutes (5100 s) at 197° C., 90 minutes (5400 s) at 250° C., then 340 minutes (20400 s) at 270° C. Thermogravimetric analysis (TGA) of a 8.45 milligram portion of the cured product was performed. Weight loss was recorded as a function of temperature at a 10° C. per minute (0.167° C./s) rate of increase in a stream of nitrogen flowing at 35 cubic centimeters per minute (0.583 cc/s). The results are reported in Table VII and can be directly compared with the results of Example 9 shown in Table VI.

TABLE VII

| Weight Loss (%) | | | | | | |
|---|---|---|---|---|---|---|
| 100° C. | 300° C. | 350° C. | 400° C. | 500° C. | 700° C. | 950° C. |
| 0 | 1.6 | 4.7 | 14.8 | 29.4 | 42.0 | 45.1 |

EXAMPLE 10

Differential Scanning Calorimetry (DSC) of a Thermally Cured Styryl Pyridine Cyanate Differential scanning calorimetry (DSC) of a 6.00 milligram portion of the cured styryl pyridine cyanate from Example 9 was performed. The analysis was completed under a nitrogen atmosphere flowing at 35 cubic centimeters per minute (0.583 cc/s) and at a scanning rate of 10° C. per minute (0.167° C./s) from 30° to 450° C. An exotherm with a midpoint of 369° C. was observed in the DSC analysis.

EXAMPLE 11

Differential Scanning Calorimetry (DSC) of an Uncured Styryl Pyridine Cyanate Differential scanning calorimetry (DSC) of a 7.20 milligram portion of the styryl pyridine cyanate from Example 3-B (uncured) was performed using the method of Example 10. An exotherm with a midpoint of 177° C. and an exotherm with a midpoint of 369° C. were observed in the DSC analysis. The 177° C. exotherm is associated with cyclotrimerization of the cyanate groups to provide triazine rings.

COMPARATIVE EXPERIMENT B

Differential Scanning Calorimetry (DSC) of a Thermally Cured Hydroxy Styryl Pyridine Differential scanning calorimetry (DSC) of a 9.90 milligram portion of the cured hydroxy styryl pyridine from Comparative Experiment A was performed using the method of Example 10. Endotherms with midpoints of 99.7° C. and 204.5° C. and exotherms with midpoints of 260° C. and 294.1° C. were observed in the DSC analysis. The small exotherm at 260° C. is associated with further curing of the hydroxy styryl pyridine. The endotherms at 99.7° C. and 204.5° C. are associated with melting of the hydroxy styryl pyridine. These results can be directly compared with the results of Examples 10 and 11.

EXAMPLE 12

Preparation of a Styryl Pyridine Cyanate

A portion of the reaction product of a 1 to 1.5 to 1 mole ratio of 2,4,6-trimethyl pyridine to p-hydroxy benzaldehyde to 2,6-dimethylpyridine (100.0 grams, 0.473 mole of hydroxy groups) from Example 3-A and acetone (750 milliliters) were added to a 2-liter glass resin kettle and maintained under a nitrogen atmosphere. Stirring was started and allowed to progress for 30 minutes (1800 s) then cooling of the reactor compound. When the reaction temperature reached −5° C., cyanogen bromide (60.12 grams, 0.568 mole) was added. After five minutes (300 s), triethylamine (57.14 grams, 0.565 mole) was added dropwise over a 23 minute (1380 s) period and so as to maintain the reaction temperature between −6° C. and 0° C. The reaction was allowed to progress for an additional 45 minutes (2700 s) between reaction temperatures of −5° C. and 0° C. After this time, the reaction slurry was filtered. The recovered filtrate was added to 1 gallon (3.79 l) of deionized water producing an amber oil precipitate. The oil product was recovered by extraction with three 500 milliliter portions of methylene chloride. The combined methylene chloride extract was washed with 1000 milliliters of deionized water, dried over anhydrous sodium sulfate and then filtered. The dry methylene chloride solution was rotary evaporated under vacuum to a constant weight of 107.40 grams. Infrared spectrophotometric analysis of a film sample of the amber colored, viscous oil product confirmed the product structure for the styryl pyridine cyanate (presence of cyanate absorbance accompanied by absence of hydroxyl group absorbance, retention of trans-unsaturation absorbance and aromatic carbon-oxygen absorbance).

EXAMPLE 13

Thermogravimetric Analysis (TGA) of a Thermally Cured Styryl Pyridine Cyanate A 0.50 gram portion of the styryl pyridine cyanate from Example 12 was cured for 2 hours (7200 s) at 240° C. Thermogravimetric analysis (TGA) of a 7.07 milligram portion of the cured product was performed. Weight loss was recorded as a function of temperature at a 10° C. per minute (0.167° C./s) rate of increase in a stream of nitrogen flowing at 35 cubic centimeters per minute (0.583 cc/s). The results are reported in Table VIII and can be directly compared with the results of Comparative Experiment A shown in Table VII.

TABLE VIII

| Weight Loss (%) | | | | | | |
|---|---|---|---|---|---|---|
| 100° C. | 300° C. | 350° C. | 400° C. | 500° C. | 700° C. | 950° C. |
| 0 | 0.6 | 1.4 | 4.3 | 19.0 | 31.5 | 35.2 |

EXAMPLE 14

Thermogravimetric Analysis (TGA) of a Series of Thermally Cured Styryl Pyridine Cyanate and N,N'-(methylenedi-p-phenylene)bismaleimide Copolymers The following series of mixtures were prepared:

| Designation | Styryl Pyridine Cyanate of Example 12 (grams) | N,N'—(methylenedi-p-phenylene)bismaleimide from Preparation 4 (grams) |
|---|---|---|
| A | 0.45 | 0.05 |
| B | 0.40 | 0.10 |
| C | 0.35 | 0.15 |

The above mixtures A, B and C were cured for 2 hours (7200 s) at 240° C. TGA of a 11.03, 6.90 and 5.96 milligram cured portion of A, B and C, respectively, was performed using the method of Example 13. The results are reported in Table IX.

TABLE IX

| Designation | Weight Loss (%) | | | | | | |
|---|---|---|---|---|---|---|---|
| | 100° C. | 300° C. | 350° C. | 400° C. | 500° C. | 700° C. | 950° C. |
| A | 0 | 0.5 | 2.6 | 9.8 | 24.5 | 37.2 | 40.2 |
| B | 0.2 | 0.8 | 3.9 | 12.6 | 26.8 | 39.6 | 43.3 |
| C | 0.2 | 0.8 | 5.9 | 15.7 | 28.5 | 43.0 | 47.2 |

EXAMPLE 15

Thermogravimetric Analysis (TGA) of a Thermally Cured Styryl Pyridine Cyanate and Vinyl Styryl Pyridine Copolymer A 0.40 gram portion of the styryl pyridine cyanate from Example 12 and 0.10 gram of a vinyl polystyryl pyridine from Preparation 1 were mixed together and then cured for 2 hours (7200 s) at 240° C. TGA of a 9.60 milligram portion of the cured product was performed using the method of Example 13. The results are reported in Table X.

TABLE X

| Weight Loss (%) | | | | | | |
|---|---|---|---|---|---|---|
| 100° C. | 300° C. | 350° C. | 400° C. | 500° C. | 700° C. | 950° C. |
| 0 | 0.1 | 0.7 | 3.6 | 18.2 | 32.0 | 34.3 |

EXAMPLE 16

Thermogravimetric Analysis (TGA) of Thermally Cured Styryl Pyridine Cyanate and Milled Carbon Fiber Composites The following series of mixtures was prepared:

| Designation | Styryl Pyridine Cyanate of Example 12 (grams) | Milled Carbon Fibers (grams) |
|---|---|---|
| A | 0.45 | 0.05 |
| B | 0.40 | 0.10 |
| C | 0.30 | 0.20 |
| D | 0.25 | 0.25 |
| Carbon Fiber (Control*) | none | 0.50 |

The milled carbon fibers used in these mixtures averaged 100 microns and were made from pitch (Kureha Carbon Fiber M-101S made by Kureha Chemical Industries Company, Ltd., Tokyo, Japan). The above mixtures A, B, C and D plus the Control (carbon fiber only) were cured for 2 hours (7200 s) at 240° C.

TGA of a 5.36, 7.93, 5.45, 9.16, and 9.92 milligram portion of A, B, C, D and the Control, respectively, was performed using the method of Example 13. The results are reported in Table XI and may be directly compared with the results obtained cured neat styryl pyridine cyanate in Example 13 and summarized in Table VIII.

TABLE XI

| Designation | Weight Loss (%) | | | | | | |
|---|---|---|---|---|---|---|---|
| | 100° C. | 300° C. | 350° C. | 400° C. | 500° C. | 700° C. | 950° C. |
| A | 0 | 0.4 | 1.8 | 7.3 | 19.8 | 31.4 | 34.0 |
| B | 0 | 0.6 | 1.2 | 4.8 | 14.8 | 25.7 | 30.0 |
| C | 0 | 0.7 | 1.8 | 4.9 | 13.9 | 24.8 | 29.0 |
| D | 0 | 0.8 | 1.1 | 3.1 | 10.9 | 20.6 | 24.1 |
| Carbon Fiber (Control*) | 0.8 | 1.4 | 1.6 | 1.9 | 2.1 | 4.2 | 9.1 |

*not an embodiment of the invention

I claim:

1. A styryl pyridine cyanate or styryl pyrazine cyanate composition resulting from cyanating a product resulting from reacting
(A) at least one of
(1) one or more pyridine compounds represented by the formula

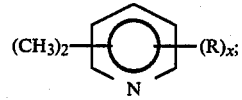

(2) one or more pyrazine compounds represented by the formula

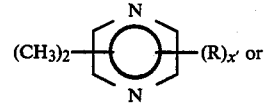

(3) a mixture of 1 and 2; with
(B) a substituted aromatic aldehyde represented by the formula

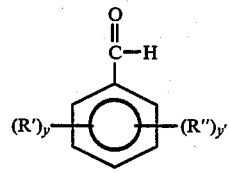

wherein each R is independently hydrogen, hydroxyl, methyl or ethyl; each R' is independently a hydroxyl or a

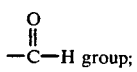

each R" is independently hydrogen, methyl or ethyl; x has a value of 3; x' has a value of 2; y has a value of 1 or 2; y' has a value of 3 or 4; the sum of y and y' has a value of 5; and with the proviso that at least one of R and R' is a hydroxyl group and wherein
  (i) components (A) and (B) are employed in quantities which provide the resultant reaction product with a reacted molar ratio of (B) to (A) of from about 0.33:1 to about 4:1 and
  (ii) at least about 1 percent of the rings in the resultant reaction product of (A) and (B) contain at least one hydroxyl group which is susceptible to being cyanated.

2. A composition of claim 1 wherein
  (i) components (A) and (B) are employed in quantities which provide the resultant reaction product with a reacted molar ratio of (B) to (A) of from about 0.5:1 to about 4:1 and
  (ii) at least about 20 to 100 percent of the rings in the resultant reaction product of (A) and (B) contain at least one hydroxyl group which is susceptible to being cyanated.

3. A composition of claim 2 wherein
  (i) components (A) and (B) are employed in quantities which provide the resultant reaction product with a reacted molar ratio of (B) to (A) of from about 0.7:1 to about 3:1 and
  (ii) at least about 30 to about 75 percent of the rings in the resultant reaction product of (A) and (B) contain at least one hydroxyl group which is susceptible to being cyanated.

4. A composition of claim 1 wherein
  (i) component (A-1) is 2,3-dimethyl pyridine, 2,4-dimethyl pyridine, 2,5-dimethyl pyridine, 2,6-dimethyl pyridine, 3,4-dimethyl pyridine, 3,5-dimethyl pyridine, 3,5-dimethyl-2-ethyl pyridine, 2,3,4,6-tetramethyl pyridine, 2,3,5-trimethyl pyridine, 2,3,6-trimethyl pyridine, 2,4,5-trimethyl pyridine, 2,4,6-trimethyl pyridine, 2,4-dimethyl-6-hydroxy pyridine, 2,6-dimethyl-4-hydroxy pyridine, 2,6-dimethyl-3-hydroxy pyridine,2,4,6-trimethyl-5-hydroxy pyridine, or a mixture therof;
  (ii) Component (A-2) is 2,5-dimethyl pyrazine, 2,3-dimethyl pyrazine, 2,6-dimethyl pyrazine, 2,3,5-trimethyl pyrazine, 2,3,5,6-tetramethyl pyrazine, 2,5-dimethyl-6-hydroxyl pyrazine, 2,5-dimethyl-3-ethyl pyrazine, or a mixture therof; and
  (iii) Component (B) is 2-hydroxy benzaldehyde, 3-hydroxy benzaldehyde, 4-hydroxy benzaldehyde, 2-hydroxy-3-methyl benzaldehyde, 2-hydroxy-3-ethyl benzaldehyde, 4-hydroxy-3,5-dimethyl benzaldehyde, terephthaldehyde, 2,6-dihydroxy benzaldehyde, methyl terephthaldehydes, dimethyl terephthaldehydes, ethyl terephthaldehydes, or a mixture therof.

5. A composition of claim 2 wherein
  (i) component (A-1) is 2,3-dimethyl pyridine, 2,4-dimethyl pyridine, 2,5-dimethyl pyridine, 2,6-dimethyl pyridine, 3,4-dimethyl pyridine, 3,5-dimethyl pyridine, 3,5-dimethyl-2-ethyl pyridine, 2,3,4,6-tetramethyl pyridine, 2,3,5-trimethyl pyridine, 2,3,6-trimethyl pyridine, 2,4,5-trimethyl pyridine, 2,4,6-trimethyl pyridine, 2,4-dimethyl-6-hydroxy pyridine, 2,6-dimethyl-4-hydroxy pyridine, 2,6-dimethyl-3-hydroxy pyridine, 2,4,6-trimethyl-5-hydroxy pyridine, or a mixture therof;
  (ii) Component (B) is 2-hydroxy benzaldehyde, 3-hydroxy benzaldehyde, 4-hydroxy benzaldehyde, 2-hydroxy-3-methyl benzaldehyde, 2-hydroxy-3-ethyl benzaldehyde, 4-hydroxy-3,5-dimethyl benzaldehyde, terephthaldehyde, 2,6-dihydroxy benzaldehyde, methyl terephthaldehydes, dimethyl terephthaldehydes, ethyl terephthaldehydes, or a mixture therof.

6. A composition of claim 3 wherein
  (i) component (A-1) is 2,6-dimethyl pyridine, 2,4,6-trimethyl pyridine or a mixture therof;
  (ii) Component (B) is 4-hydroxy benzaldehyde.

7. A polymer prepared by polymerizing one or more cyanated composition of claim 1.

8. A polymer prepared by polymerizing one or more cyanated composition of claim 2.

9. A polymer prepared by polymerizing one or more cyanated composition of claim 3.

10. A polymer prepared by polymerizing one or more cyanated composition of claim 4.

11. A polymer prepared by polymerizing one or more cyanated composition of claim 5.

12. A polymer prepared by polymerizing one or more cyanated composition of claim 6.

13. A polymerizable or curable mixture of
  (A) at least one of the aforementioned styryl pyridine cyanates, styryl pyrazine cyanates or combination thereof of claims 1, 2, 3, 4, 5 or 6; and
  (B) at least one material selected from
    (1) (a) styryl pyridines, (b) styryl pyridine prepolymers, (c) styryl pyridine polymers or (d) any combination thereof;
    (2) (a) vinyl styryl pyridines, (b) vinyl styryl pyridine prepolymers, (c) vinyl styryl pyridine polymers or (d) any combinatioin thereof;
    (3) alkenyl phenyl cyanates;
    (4) (a) dicyanates, (b) polycyanates or (c) any combination thereof;
    (5) (a) bismaleimides, (b) polymaleimides or (c) any combination thereof;
    (6) epoxy resins;
    (7) (a) alkenyl phenol capped styryl pyridines, (b) alkenyl phenol capped styryl pyridine prepolymers, (c) alkenyl phenol capped styryl pyridine polymers or (d) any combination thereof; or
    (8) mixtures thereof in any proportion and combination.

14. A polymerizable or curable mixture of claim 13 wherein component (B-2) is a vinyl polystyryl pyridine prepared from 2,4,6-trimethyl pyridine, terephthaldehyde and 2-methyl-5-vinyl pyridine.

15. A polymerizable or curable mixture of claim 13 wherein
  (i) component (B-3) is p-isopropenylphenyl cyanate and
  (ii) component (B-4) is bisphenol A dicyanate.

16. A polymerizable or curable mixture of claim 13 wherein component (B-6) is a diglycidyl ether of bisphenol A.

17. A polymerizable or curable mixture of claim 13 wherein component (B-5) is N,N'-(methylenedi-p-phenylene)bismaleimide.

18. Products resulting from polymerization and/or curing of a composition of claim 13.

19. Products resulting from polymerization and/or curing of a composition of claim 14.

20. Products resulting from polymerization and/or curing of a composition of claim 15.

21. Products resulting from polymerization and/or curing of a composition of claim 16.

22. Products resulting from polymerization and/or curing of a composition of claim 17.

23. An article prepared from a polymer of claim 7.

24. An article prepared from a polymer of claim 8.
25. An article prepared from a polymer of claim 9.
26. An article prepared from a polymer of claim 10.
27. An article prepared from a polymer of claim 11.
28. An article prepared from a polymer of claim 12.
29. An article prepared from a product of claim 18.
30. An article prepared from a product of claim 19.
31. An article prepared from a product of claim 20.
32. An article prepared from a product of claim 21.
33. An article prepared from a product of claim 22.

* * * * *